(12) United States Patent
Lewkonya et al.

(10) Patent No.: US 9,844,634 B2
(45) Date of Patent: Dec. 19, 2017

(54) AUTOMATIC NEEDLE APPARATUS

(71) Applicant: DALI Medical Devices LTD., Yavne (IL)

(72) Inventors: Gad Lewkonya, Neve Mivtach (IL); David Daily, Herzliya (IL); Lior Raday, MP Hof Ashkelon (IL)

(73) Assignee: DALI MEDICAL DEVICES LTD., Yavne (IL)

( * ) Notice: Subject to any disclaimer, the term of this patent is extended or adjusted under 35 U.S.C. 154(b) by 153 days.

(21) Appl. No.: 14/505,690

(22) Filed: Oct. 3, 2014

(65) Prior Publication Data
US 2016/0095983 A1 Apr. 7, 2016

(51) Int. Cl.
*A61M 5/32* (2006.01)
*A61M 5/31* (2006.01)
A61M 5/34 (2006.01)
A61M 5/42 (2006.01)

(52) U.S. Cl.
CPC .......... *A61M 5/3257* (2013.01); *A61M 5/31* (2013.01); *A61M 5/321* (2013.01); *A61M 5/326* (2013.01); *A61M 5/3243* (2013.01); *A61M 5/3287* (2013.01); *A61M 5/3202* (2013.01); *A61M 5/347* (2013.01); *A61M 5/425* (2013.01); *A61M 2005/3247* (2013.01); *A61M 2005/3267* (2013.01)

(58) Field of Classification Search
CPC .... A61M 5/3257; A61M 5/31; A61M 5/3287; A61M 5/321; A61M 5/3243; A61M 5/326; A61M 5/3202; A61M 5/347; A61M 5/425; A61M 2005/3247; A61M 2005/3267
See application file for complete search history.

(56) References Cited

U.S. PATENT DOCUMENTS

| | | | | |
|---|---|---|---|---|
| 6,322,540 B1 * | 11/2001 | Grabis | ............... | A61M 5/3257 604/110 |
| 2007/0118081 A1 * | 5/2007 | Daily | ................... | A61M 5/326 604/198 |
| 2011/0288491 A1 * | 11/2011 | Newman | ............... | A61M 5/326 604/198 |

* cited by examiner

*Primary Examiner* — Kevin C Sirmons
*Assistant Examiner* — Amber Stiles

(57) ABSTRACT

An automatic needle device comprises a body into which a needle assembly and needle are mounted. The device also includes a needle guard to cover the needle until it is used and to lock over the needle after use so the needle is not re-exposed. The locking is accomplished with a coil spring action locking device. A container for holding the automatic needle device also facilitates the viewing of the distal end of the needle prior to use on a patient.

9 Claims, 21 Drawing Sheets

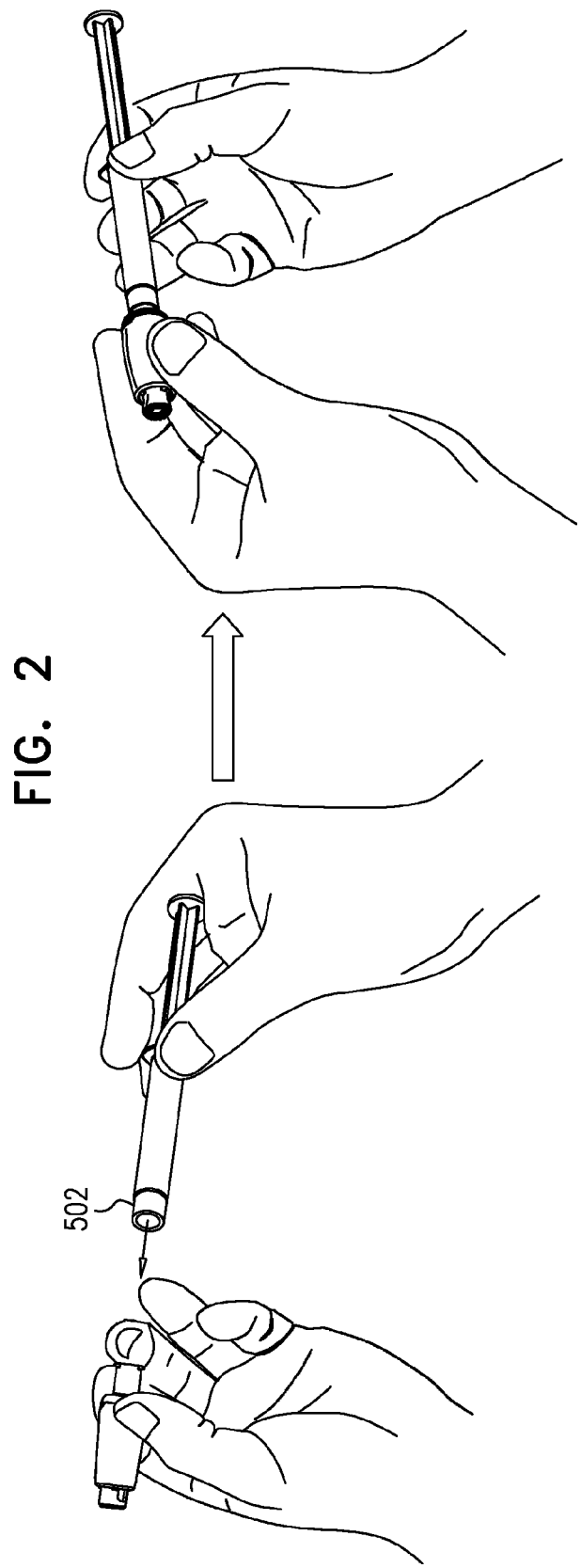

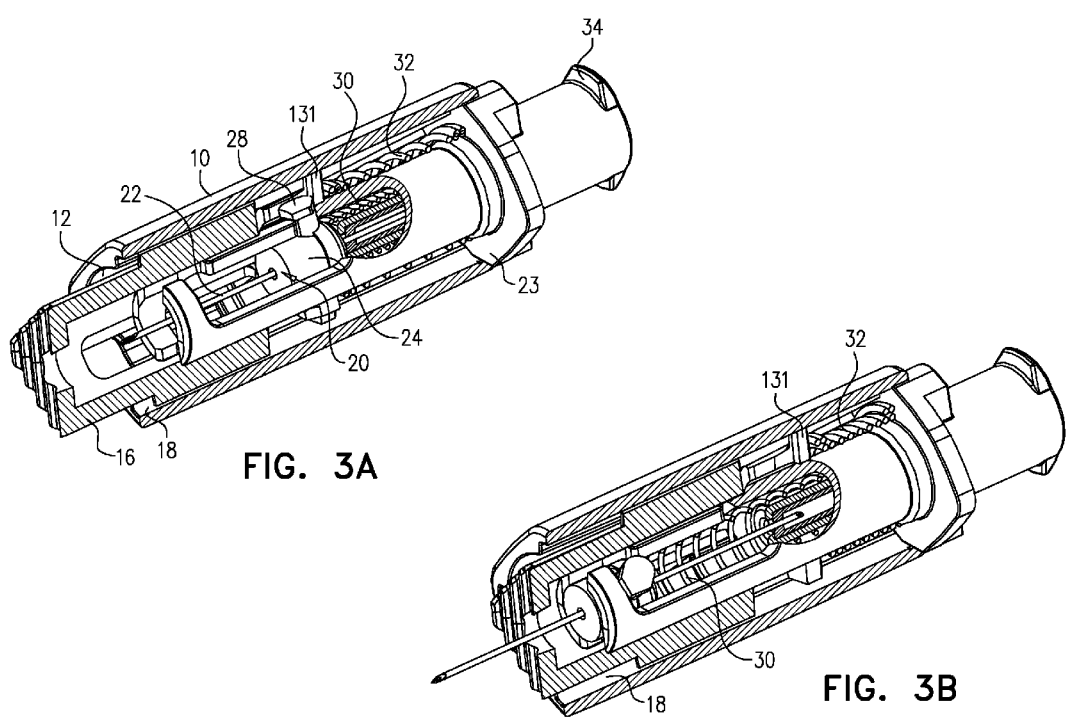

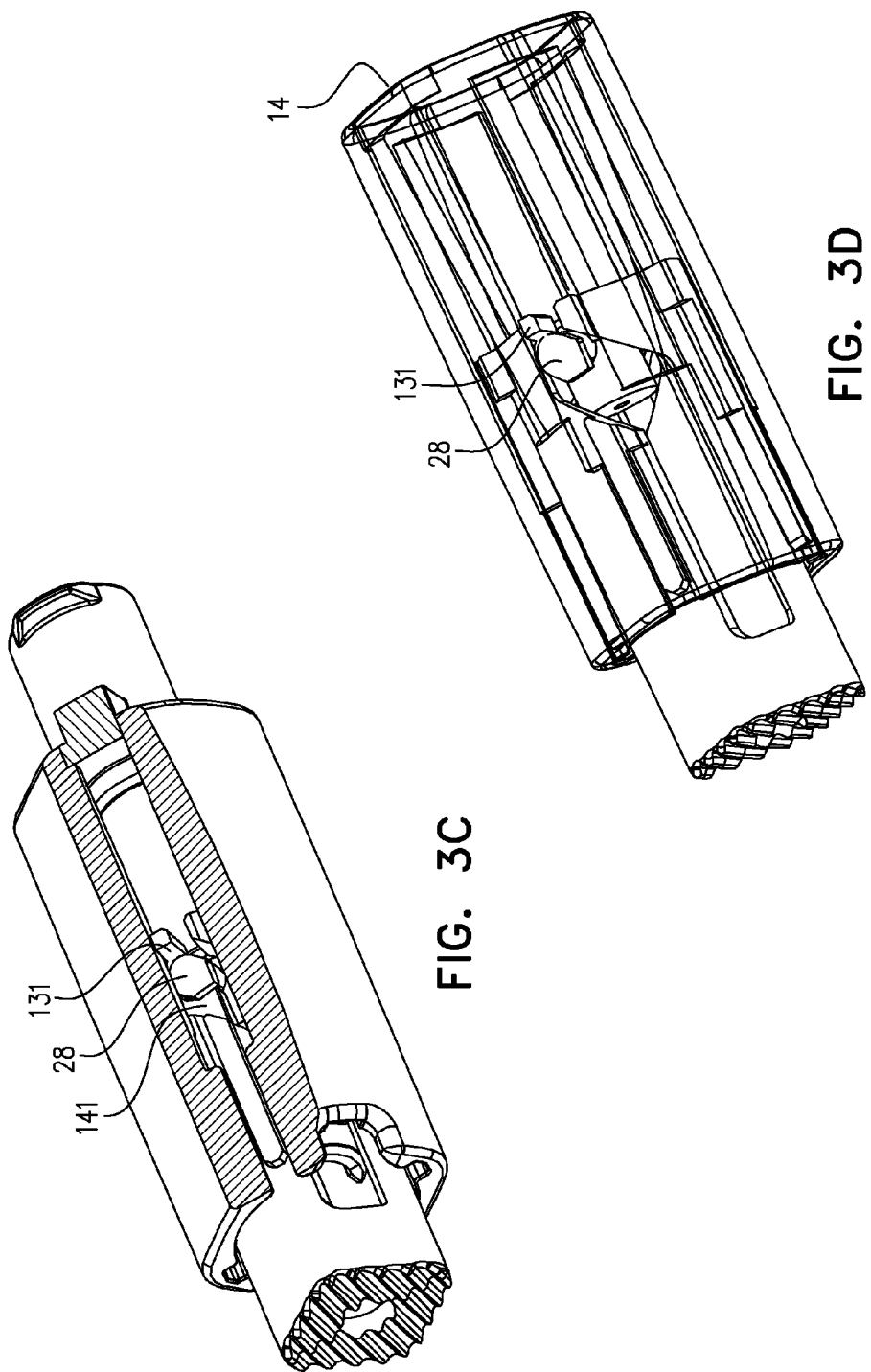

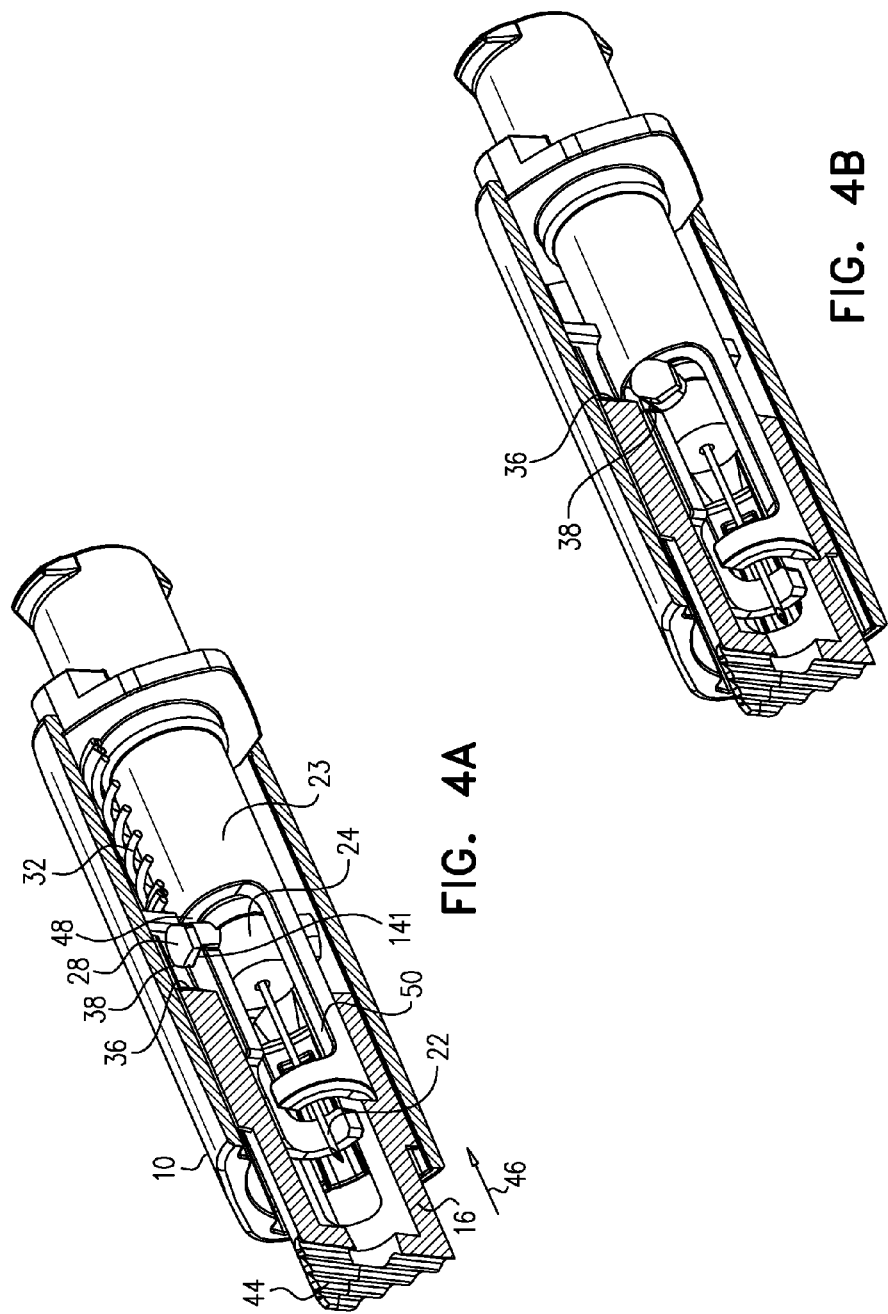

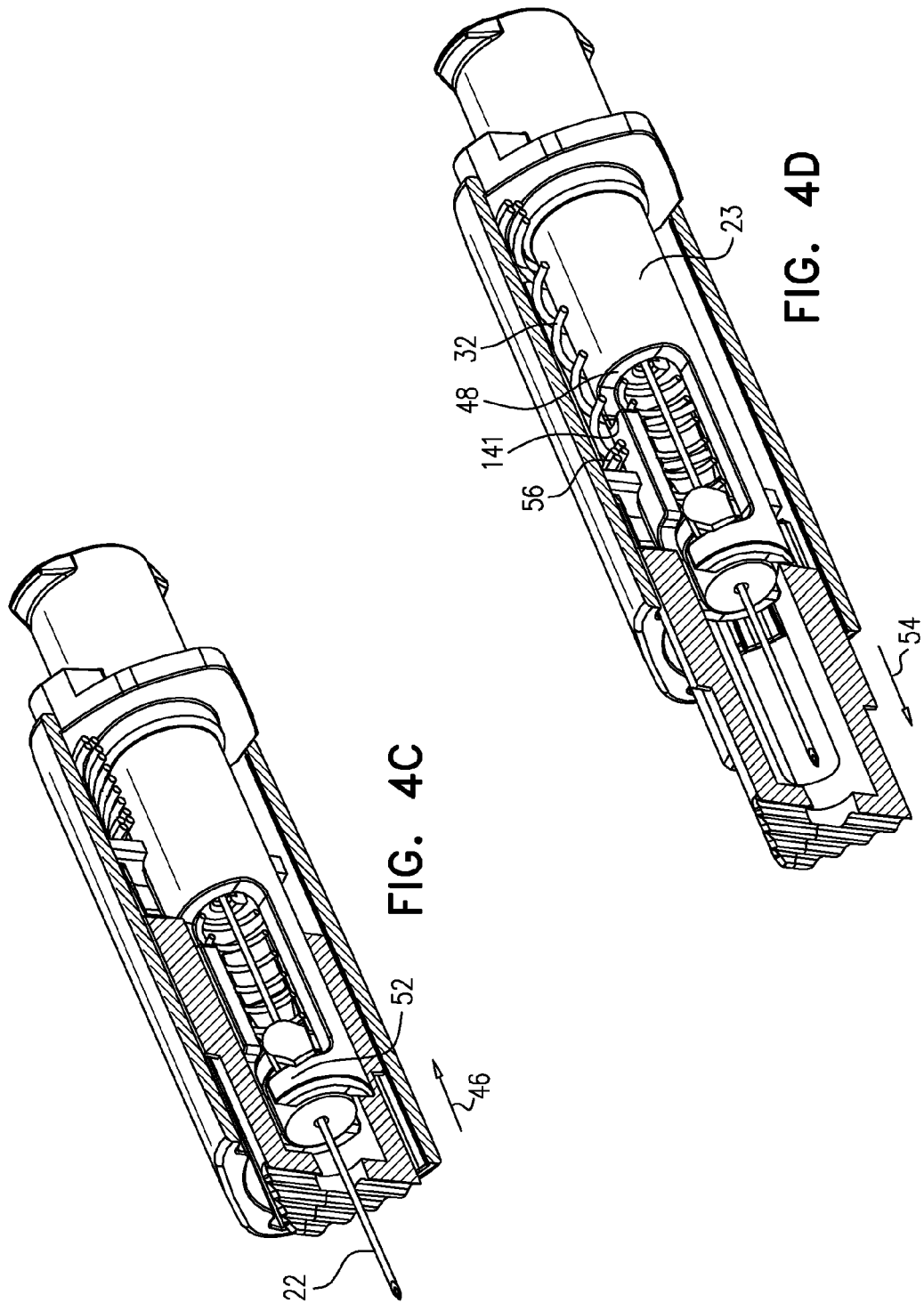

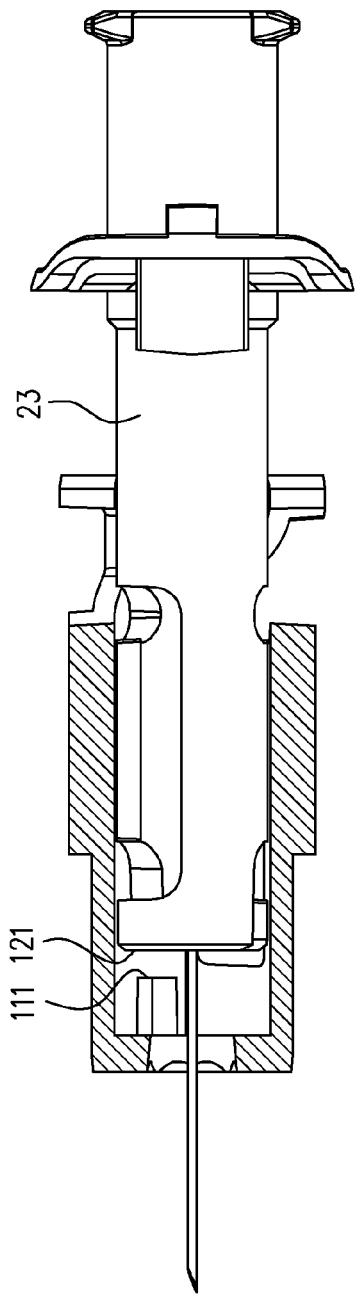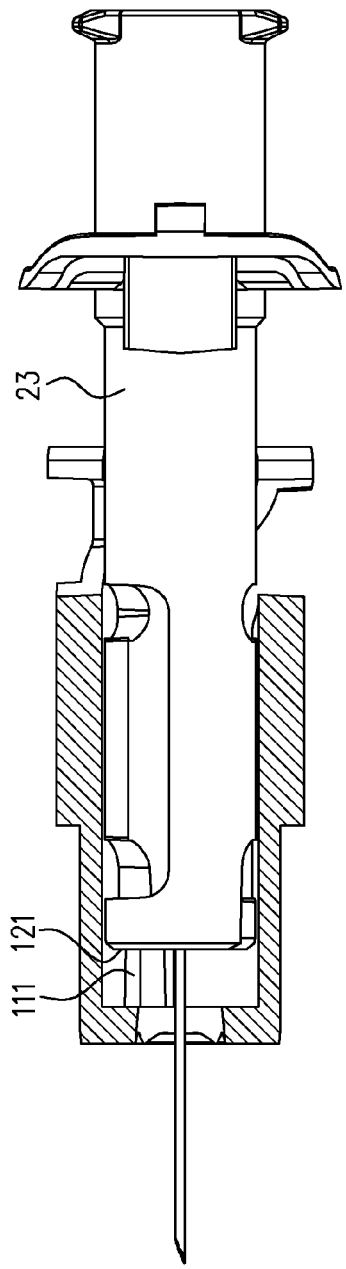

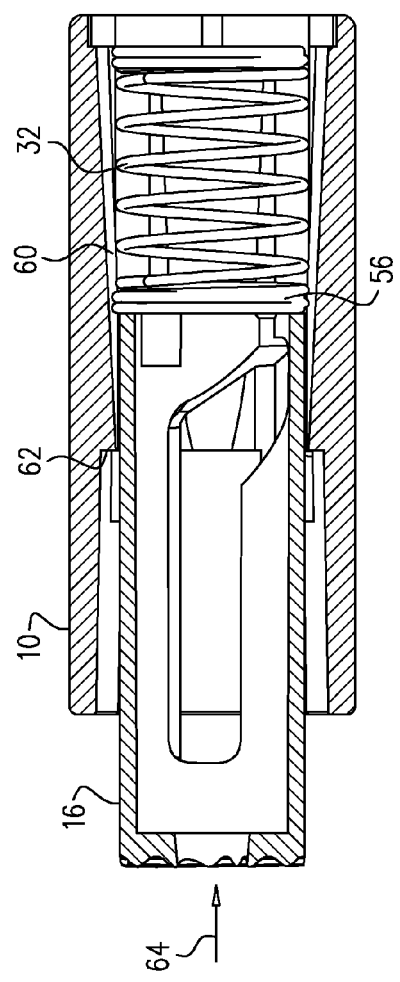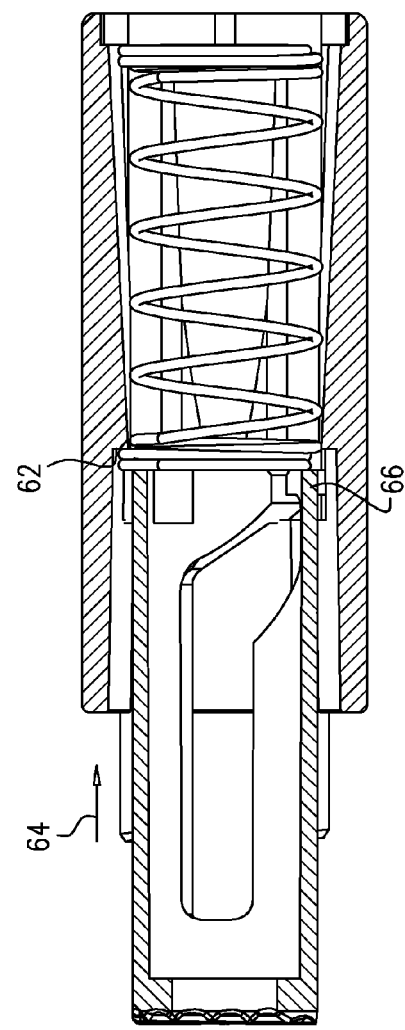

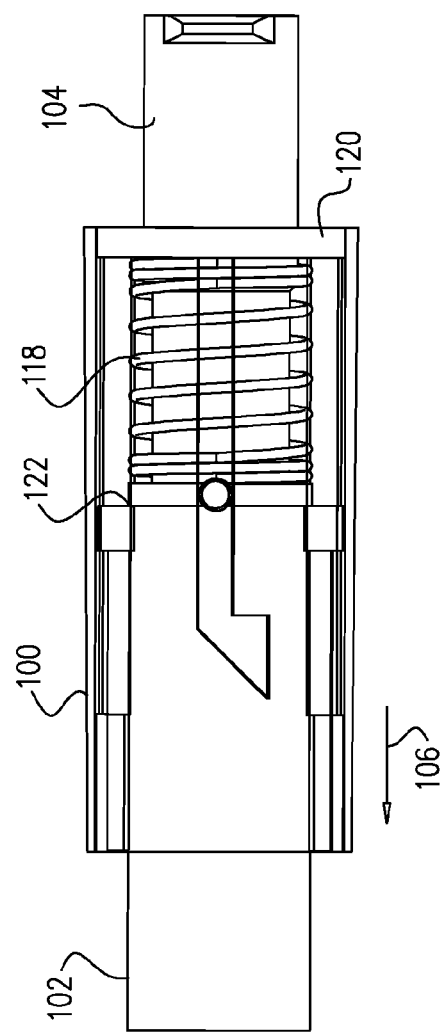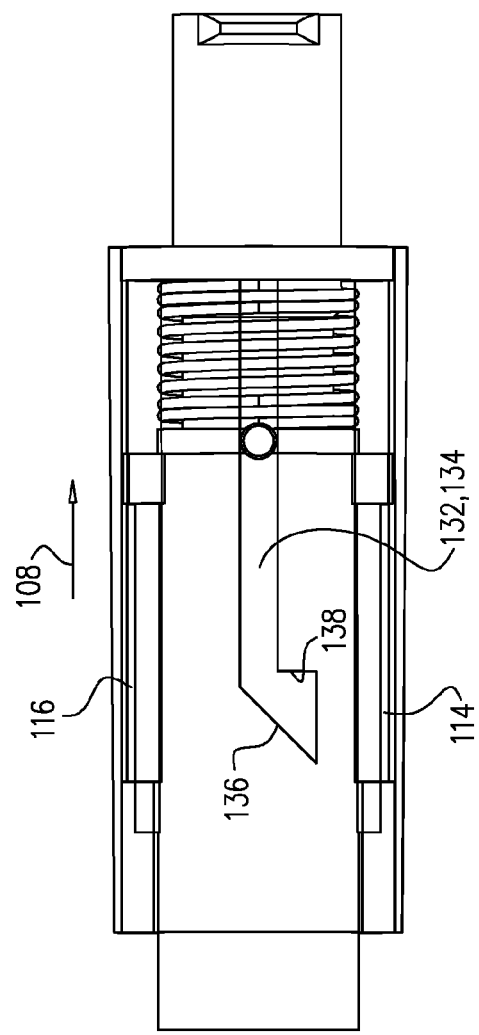

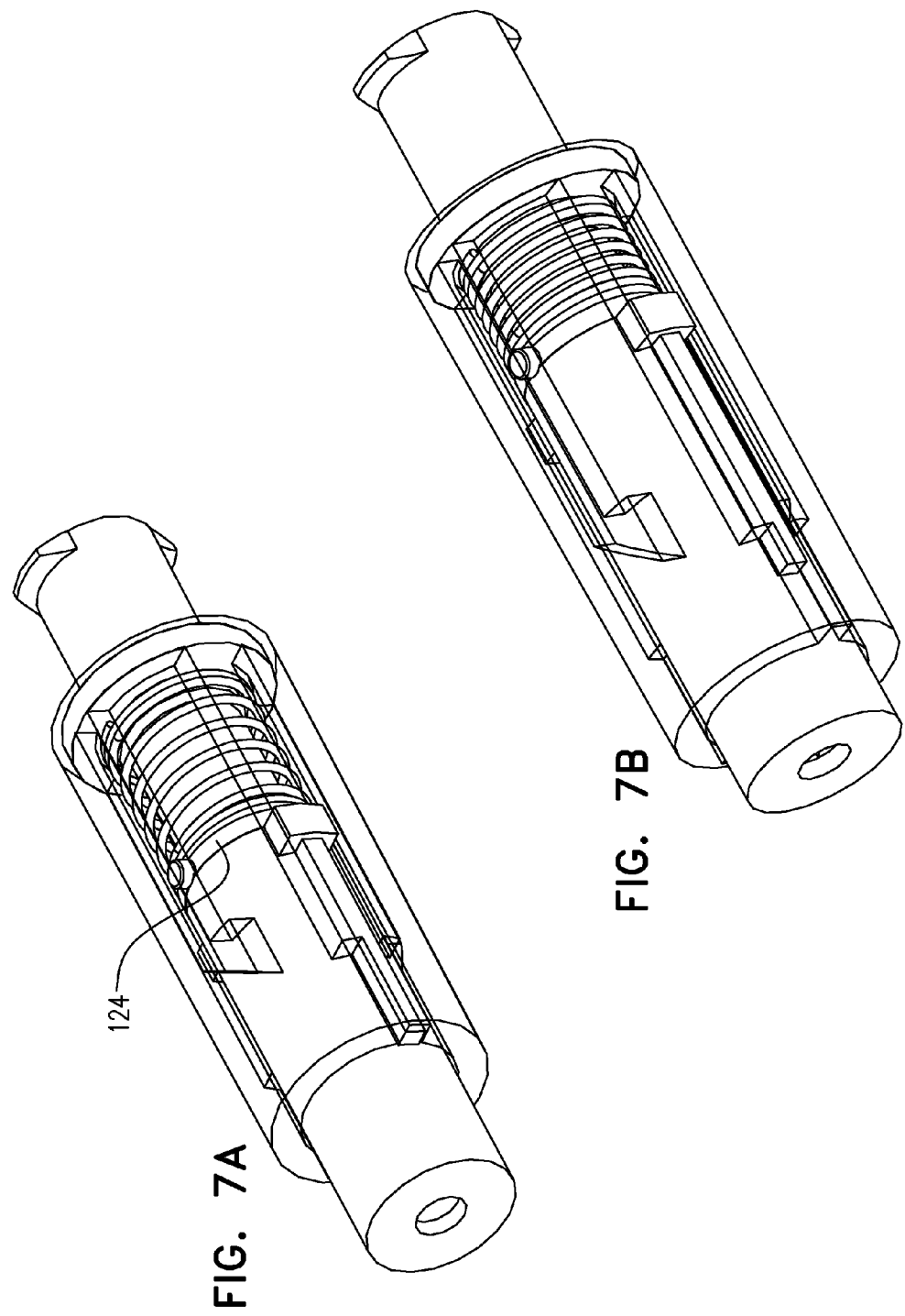

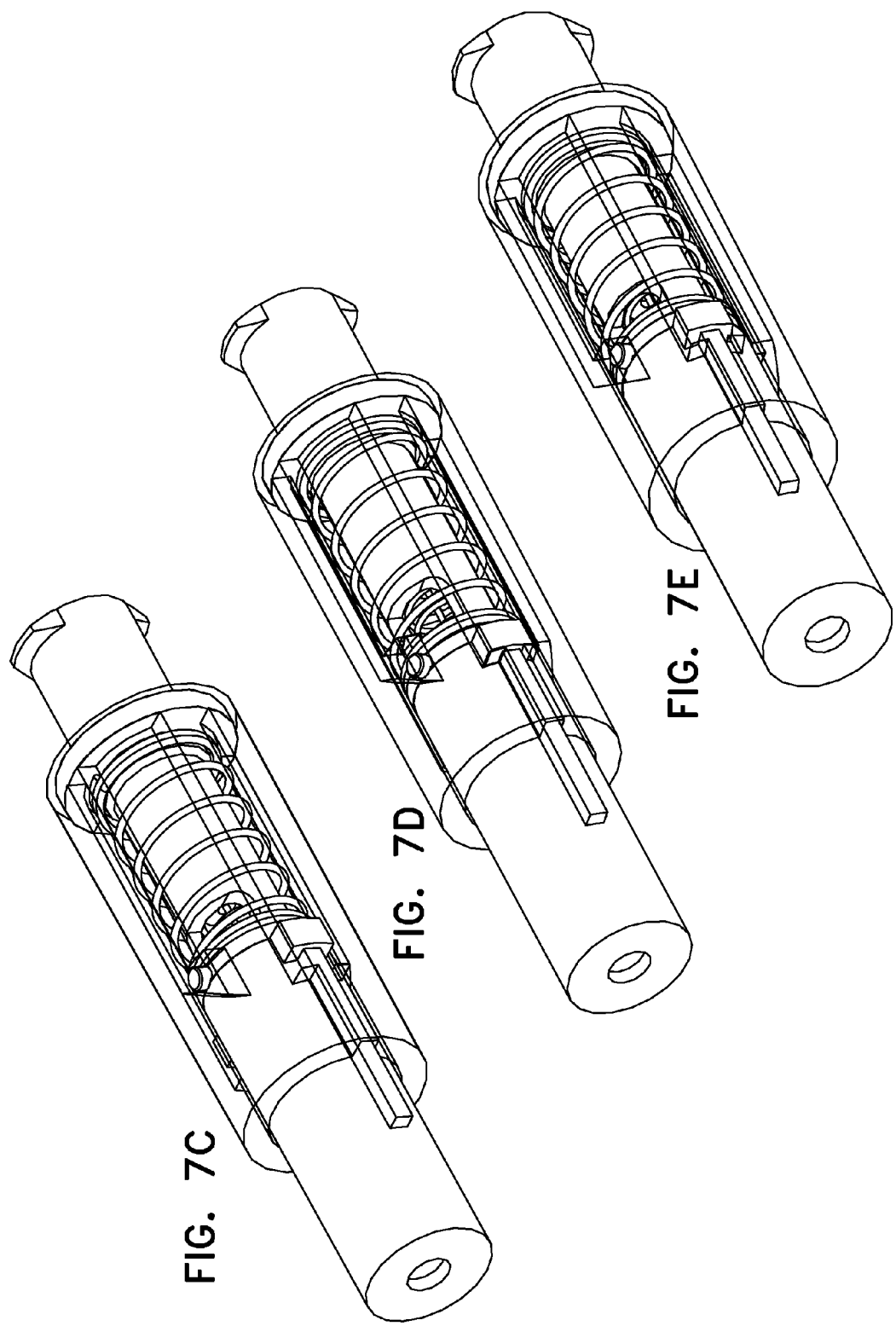

AUTOMATIC NEEDLE APPARATUS

FIELD OF THE INVENTION

The present invention relates to hypodermic syringes and in particular to automatic needle apparatus which are attachable to hypodermic syringes.

BACKGROUND OF THE PRESENT INVENTION

Automatic needle apparatus and devices are known in the art. One example of such a needle device is embodied in U.S. Pat. Nos. 7,901,382 and 8,328,765, both entitled "Automatic Needle Device" and are assigned to the assignee of the present invention. The entirety of such U.S. Pat. Nos. 7,901,382 and 8,328,765 are incorporated herein by reference. This application is also related to U.S. Design application Ser. No. 29/471,756, filed Nov. 5, 2013, entitled "Automatic Needle Device", the entirety of which application is herein incorporated by reference.

A concern with the use of such needle devices is that the needle be made to exit from the device housing and be deployed in a safe condition, and then have the needle guard deployed to cover the needle and essentially become locked therein so that the needle is not able to be re-deployed for the sake of preventing contamination and potential injury to the user or any other person by being "stuck" with the needle again.

Thus, there is a need in the industry for a simple needle device which is easily deployable and cannot be re-deployed. It is to this that the present invention is directed.

SUMMARY OF THE INVENTION

In one aspect, an automatic needle device is attachable to an injection device comprising a housing element having distal and proximal ends. The proximal end of the housing element has a connector adapted for attachment to the injection device wherein a needle assembly is at least partly within the housing element. The needle assembly has a needle extending from the distal end of the needle assembly wherein a needle guard has distal and proximal ends. The needle guard is positioned in the distal end of the housing element and movable from a first extended position to a retracted position to a second extended position. The needle guard covers the needle in the first and the second extended positions and exposes the needle in the retracted position. The needle guard is biased by a biasing device in a distal direction and is retracted to the retracted position upon contact of the distal end of the needle guard with a surface. The biasing device comprises a coil spring having distal and proximal ends and a locking mechanism. The locking mechanism locks the needle guard in the second extended position when the needle guard, under the influence of the biasing device, moves to the second extended position. One of the coil spring distal end pushes the proximal end or the distal end of the needle guard and is positioned in an interior locking surface within the housing element. When the needle guard moves to the second extended position, whereby the needle guard is locked in the second extended position. Alternatively, the coil spring distal end pushes against a locking ring proximal surface, the locking ring distal surface pushes the needle guard proximal end. The locking ring further comprises one or more locking pins engaging an interior surface within the housing when the needle guard moves to the second extended position, whereby the needle guard is locked in the second extended position.

In another aspect, the device has one or more of the coils in the distal end of the coil spring which are offset from the remaining coils of the coil spring. The one or more offset coils are positioned in the interior locking surface within the housing unit when the needle guard moves to the second extended position.

In yet another aspect, the device has one or more of the offset coils in the distal end which may have a tighter pitch compared to the remaining coils of the coil spring.

In another aspect, the device has one or more locking pins which slide within one or more corresponding grooves within the interior surface of the housing element, the one or more grooves each having a slot at the distal end of the one or more grooves, each slot receiving the one or more locking pins when the needle guard moves to its second extended position.

In another aspect, the device has two locking pins two grooves and the locking pins are moved in a distal direction and axially turned to be positioned into two slots to lock the needle guard.

In one aspect, the automatic needle device has a needle guard which additionally has a plurality of side walls connecting the distal end and the proximal end and the side walls are apertured with at least one opening in at least one of the side walls to allow a user to view the needle distal end.

In another aspect, the automatic needle device has a needle guard which additionally has a plurality of side walls connecting the distal end and the proximal end and at least one of the needle guard side walls are of a substantially transparent material to allow a user to view the needle distal end.

In an aspect, the device has openings which are one of polygonally or curved shaped.

In yet another aspect, an outer housing container is adapted to house the automatic needle device, and includes distal and proximal ends, the proximal end being open to accept and house the automatic needle device. The distal end is closed, and the housing container further includes side walls joining the distal and proximal ends. The side walls are structured so as to enable viewing of the distal end of the needle in the automatic needle device.

In another aspect, the outer housing container has the outer housing which is constructed of a substantially transparent material to enable viewing of the needle distal end.

In yet another aspect, the housing has at least one of the side walls of the housing container which is apertured with at least one opening in at least one of the side walls to enable viewing of the needle distal end.

In another aspect, the container has one or more guiding devices within the interior of the side walls of the container such that, upon insertion of the automatic needle device into the container, the apertures on the needle guard are aligned with the apertures on the container.

In yet another aspect, the container has an optical structure which is inserted into or formed onto the at least one of the side wall aperture, the optical structure facilitating the viewing of the needle distal end.

In another aspect, the container has the optical structure which comprises either a lens structure or a prism structure, or a combination of a lens structure and a prism structure.

In another aspect, the container has an optical structure which is formed onto the outer housing container to enable viewing of the needle distal end.

In one aspect, the container structure has the optical structure which redirects light in a direction towards the needle distal end.

In another aspect, an outer housing container is adapted to house an automatic needle device, has a needle device with a needle and a distal end, and the housing container includes distal and proximal ends. The proximal end is open to accept and house the needle device. The distal end is closed. The housing container further includes side walls joining the distal and proximal ends, the side walls being structured so as to enable viewing of the distal end of the needle of the needle device.

In another aspect, an outer housing container is adapted to house an automatic needle device, has a needle device with a needle and a distal end, and the housing container includes distal and proximal ends. The proximal end is open to accept and house the needle device. The distal end is apertured. The housing container further includes side walls joining the distal and proximal ends. The apertured end enables viewing of the needle device distal end.

In an aspect, the container has a lens which is one of attached to or formed with the distal end of the container to facilitate end-on viewing of the needle device distal end.

In another aspect, the container has one or more of a right prism or a lens which is one of attached to or formed with the distal end of the container to facilitate side-on viewing of the needle device distal end.

In yet another aspect, an outer housing container is adapted to house an automatic needle device. The needle device has a needle with a distal end, wherein the housing container includes distal and proximal ends. The proximal end is open to accept and house the needle device. The distal end is closed. The housing container further includes side walls joining the distal and proximal ends, the housing container being substantially transparent to enable viewing of the needle device distal end. The outer housing container may have features or textures to guide the user to locate the needle tip viewing area. E.g., having all the outer housing container with opaque surface and only the viewing area clear/transparent.

BRIEF DESCRIPTION OF THE DRAWING FIGURES

Embodiments of the present invention are described by way of example only with reference to the accompanying drawings, wherein:

FIGS. 1 and 2 illustrate a first embodiment of a needle injection device of the present invention.

FIGS. 3A and 3B illustrate a first embodiment of the present invention.

FIGS. 3C and 3D illustrate the structure and operation of a hub and slot arrangement.

FIGS. 4A to 4F illustrate the sequence of operations in the deployment of the needle device of FIGS. 3A and 3B.

FIGS. 5A to 5E illustrate the operation of a first embodiment of a locking mechanism in accordance with the present invention.

FIGS. 6A to 6E illustrate an alternative embodiment of the present invention.

FIGS. 7A to 7E illustrate another view of the embodiment of FIGS. 6A to 6E.

DETAILED DESCRIPTION OF THE PRESENT INVENTION

Figure 1:
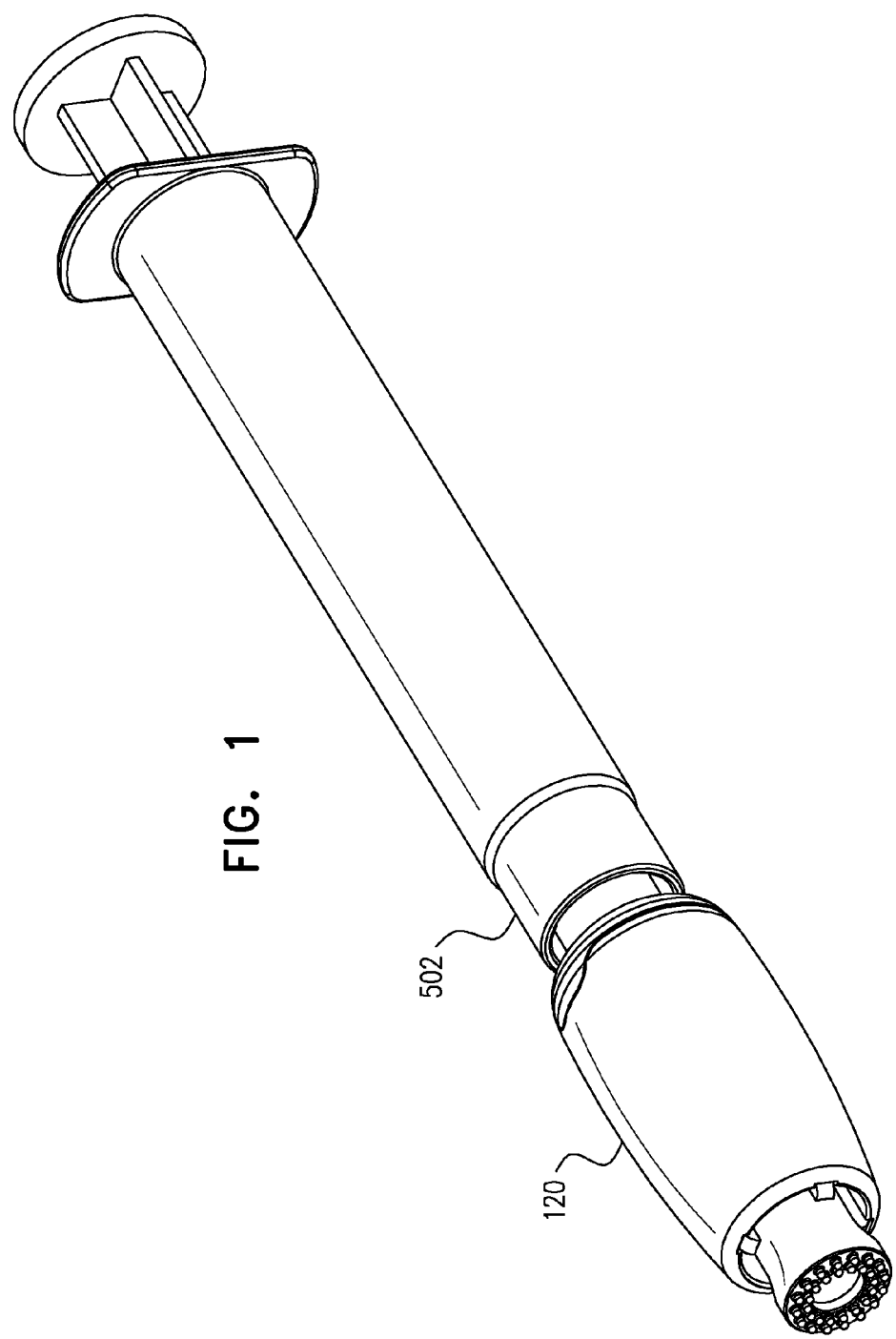

As shown in FIG. 1, a device 120 containing an injection needle is attachable to a hypodermic syringe body 502. FIG. 2 is another view of the device and illustrates the sequence by which the needle device is attached to the hypodermic syringe 502.

Turning now to FIGS. 3A, 3B and 4D, these figures broadly illustrate the position of a needle guard in a first embodiment of the present invention in a first extended, stored/pre-use condition (FIG. 3A), in a needle deployed condition but guard retracted position (FIG. 3B), and a second extended condition (FIG. 4D).

In FIG. 3A, a main housing 10 is in the form of an open-ended tube-like structure with a distal end opening 12 and a proximal end opening 14 (shown in FIG. 3D). A number of components are located coaxially within the housing. These include a needle guard 16 which is located in the distal portion of the housing and is movable from a first extended position as seen in FIG. 3A to a retracted position as seen in FIG. 3B. The needle guard 16 slides within the body housing along grooves 18 but is constrained in movement in a distal direction by stop 131 so that the guard rests on protrusion 28 of needle hub 24. The needle guard is not constrained in movement in a proximal direction. The needle guard is urged in a distal direction by a needle guard spring 32.

Main housing 10 includes a needle hub assembly 20 which includes a needle 22 and needle hub 24. The needle hub assembly and septum are structurally similar to that same structure described and shown in U.S. Pat. No. 8,328, 765 (see col. 12, lines 12-22; FIG. 1, elements 30, 32, 34 and 36). The descriptions and drawings from the aforesaid patent are, as noted above, incorporated by reference and do not form a specific portion of the present invention per se. However, the needle hub 24 of the present invention shown in FIG. 3A is located in a luer housing 23 and includes a tab or protrusion 28, the operation of which will be described below in connection with FIGS. 4A to 4D. In addition, a luer-type lock connection 34 is formed on the proximal part of the luer housing 23 to facilitate attachment to a hypodermic syringe or another injection device. Luer housing 23 may be a separate module from the housing 10 with which it is placed and may either be removable or may preferably be glued or otherwise fixed with housing 10 so that they form one unitary structure. Housing 10 and Luer housing 23 may also be constructed or assembled differently as known to the skilled man in the art.

Device 120 also includes two coil springs, hub spring 30 and needle guard spring 32. In FIG. 3A, it can be seen that hub spring 30 is in a relatively compressed state and in FIG. 3B in a relatively less compressed state. In general, hub spring 30 is responsible for causing the needle hub assembly 20 to move, using the force of the hub spring 30 from a retracted position as in FIG. 3A to an extended needle position as seen in FIG. 3B. FIG. 3A shows the needle device with components positioned prior to use and FIG. 3B shows the needle device with components positioned when put in use in a needle deployed position, to be explained below in detail.

Turning now to FIGS. 4A to 4F, these figures illustrate the operation of the embodiment of FIG. 3A. FIG. 4A shows the assembly in its non-activated or initial stored or pre-use position. In this position the needle is recessed within the needle guard 16 which is in its first extended position. Needle hub assembly 20 is constrained from movement distally despite the hub spring 30 (not shown in FIG. 4A) due to its tab 28 resting against the stop 141 of luer housing 23.

In use, after the needle device is attached to a hypodermic syringe, the needle guard is positioned over the patient's skin surface and lowered until the distal portion 44 of the needle guard comes into contact with the skin surface. As illustrated in FIGS. 3C and 3D, these figures show the hub 24 in its pre-deployed position wherein hub protrusion 28 of the hub 24 abuts stop 141 which constrains its movement in a distal direction. The hub 24 is not constrained in movement in a proximal direction. The hub is urged in a distal direction by a hub spring 30 and needle guard spring 32 that urges the needle guard 16 which rests through its stop 131 on protrusion 28 of needle hub 24. (see also another view in FIG. 3D). Hub 24 is urged by hub spring 30 in a distal direction. As noted, the needle guard is movable in a proximal direction within the housing 10 against the resistance of needle guard spring 32. As the distal portion 44 of the needle guard is further pressed into the skin surface, this causes the needle guard to move in direction 46 as seen in FIG. 4A. As it does so, the cam surface 36 of needle guard 16 is also moved in direction 46 and comes into contact with hub cam surface 38, as seen in FIG. 4B. Further movement of the needle guard 16 in direction 46 results in the hub 24 and its tab or protrusion 28 being forced out of its slot 48 and rotated about the hub's axis. Once the tab is moved out of slot 48, it is in alignment with second slot 50 of the luer housing 23. Once in second slot 50, hub 24 is no longer constrained in its axial movement and will move in a distal direction within the slot 50 until it reaches an abutment 52 as seen in FIG. 4C under the compressive force of the hub spring 30. FIG. 4C illustrates the needle device in its deployed needle penetration position in the patient's skin and ready for the material in an attached hypodermic syringe to be injected into the patient. FIGS. 4E and 4F illustrate the needle in the deployed position and in which the distal end 121 of the luer housing 23 is seen in FIG. 4F to abut a protrusion 111 of the needle guard 16. This interaction limits the amount by which the needle extends beyond the distal end of the needle guard and thus fixes the depth of penetration of the needle into the patient's skin. The size of the protrusion 111 may be factory adjusted to a desired size to control the depth of skin penetration. The needle penetration depth may also be adjusted, for example, by the length of the needle or for example by the length of slot 50 or the overall length of needle guard 16 or by any combination thereof.

Figure 9A:
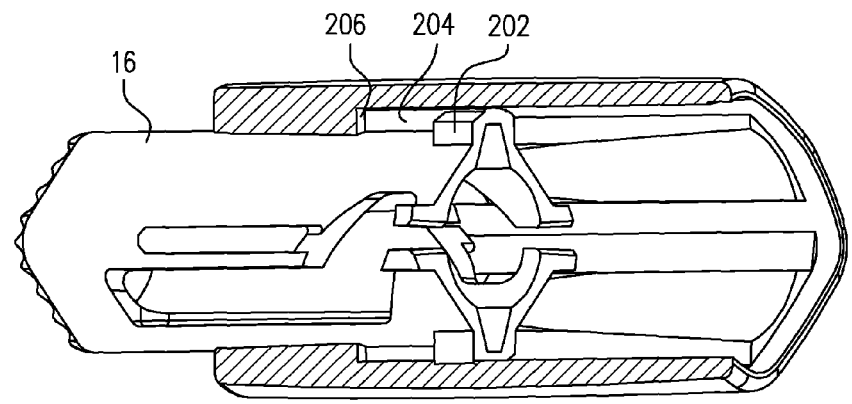
FIGS. 9A to 9C illustrate the structure and operation of a needle guard within a housing.
Figure 9B:
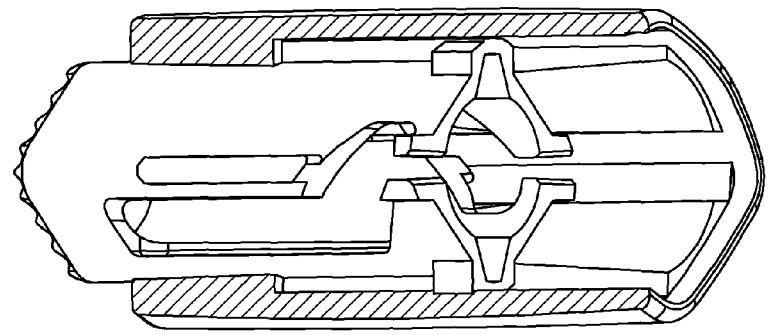
Figure 9C:
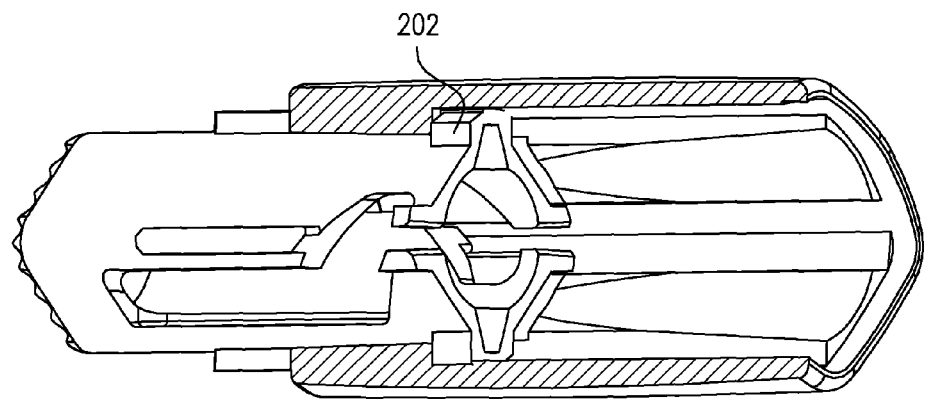

FIGS. 9A to 9C illustrate the movement of the needle guard between its first, second and third positions as discussed above in sequence. In FIG. 9A, the needle guard 16 is in its first extended position in which a needle guard block 202 within a slot 204 is not in contact with a housing sleeve block 206. In the second position of FIG. 9B, the needle guard is being moved in proximal direction by being in contact with the patient's skin surface. In FIG. 9C, the third position, the needle block guard 202 is in contact with the housing sleeve block 206 in its second extended position.

After injection, the hypodermic syringe may be raised from its position in FIG. 4C. Upon that occurrence, the needle guard is moved in a direction 54 as seen in FIG. 4D and does so under the influence of needle guard spring 32, which, has been kept in its relatively more compressed state of FIG. 4C. The relative decompression of the needle guard spring 32 causes the needle guard to cover the needle 22 shown as protruding in FIG. 4C to a position in which it is covered as seen in FIG. 4D. However, it would be useful to provide a locking device to prevent, for example, the needle guard being accidentally pushed in direction 46 and the needle becoming exposed. Thus, with the needle guard covered and locked, potential contamination or the possibility of someone being "stuck" by the needle is prevented.

Figure 5A:
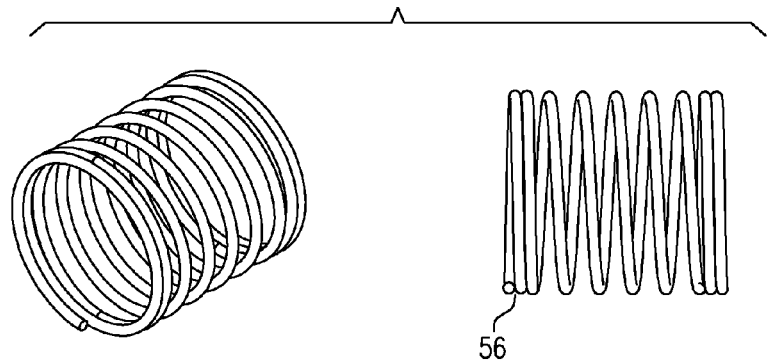
Figure 5B:
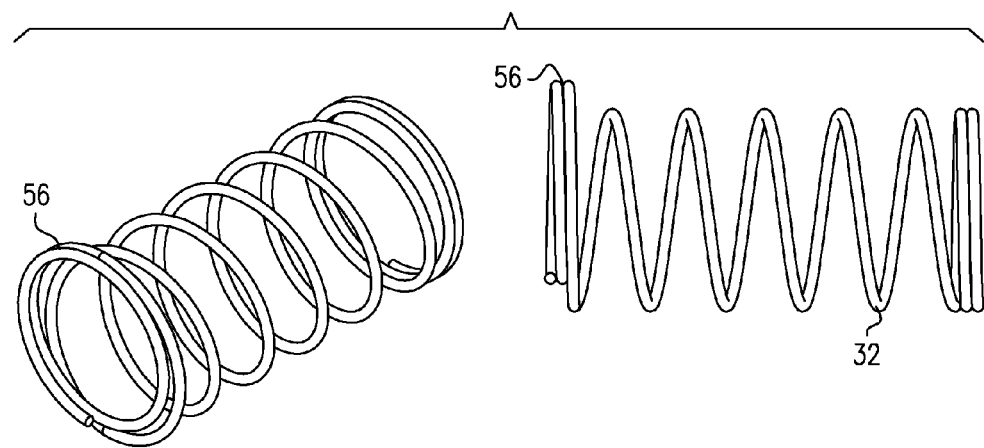
Figure 5E:
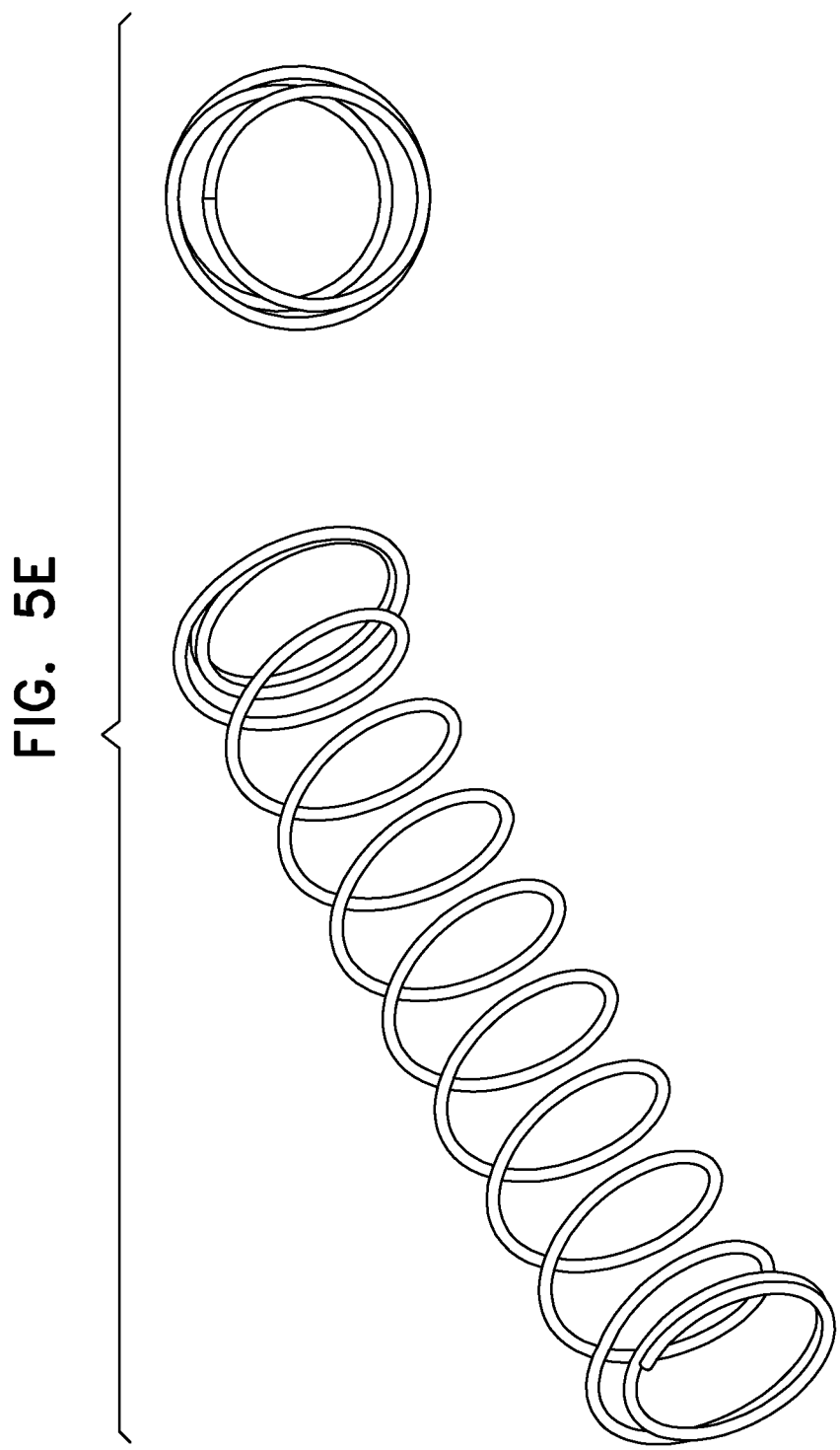

To this end, a locking mechanism may be provided to prevent the needle from being reexposed. FIG. 4D illustrates the needle guard spring 32. Needle guard spring 32 has a distal end 56 as shown in FIG. 4D. Turning now to FIGS. 5 and 6, these figures illustrate the operation of locking mechanisms in the present embodiment. Needle guard spring 32 is shown in its compressed state and relatively uncompressed state in FIGS. 5A and 5B respectively. Needle guard spring 32 may have a distal end 56 which is shown in FIGS. 5A and 5B as comprising at least one tightly bunched offset coil. FIGS. 5C and 5D are simplified illustrations of the operation of the locking mechanism of this embodiment using spring 32. As can be seen, the end coils are offset from the axis of the other coils. This feature is illustrated in FIGS. 5A and 5B, but also shown in FIG. 5E.

FIG. 5C shows the needle guard spring 32 in its relatively compressed position (the same position as the needle guard spring 32 appears in FIG. 4A). Within the body 10 is an interior surrounding incline 60 which increases in height in a distal direction as can be seen in FIG. 5C. At the end of the incline is a step 62 formed in housing 10. As the needle guard 16 moves from a position of FIG. 5C to 5D, the distal end 56 of the needle guard spring 32 moves along the incline 60 until the end of the needle guard spring 56 drops into the step 62 due to the offset of the spring end 56. Incline 60 reduces the friction between the offset spring coils and the inclined wall as the needle guard is compressed in a proximal direction 64. When the spring end 56 is in its position shown in FIG. 5D, the proximal end 66 of the guard 16 abuts the spring end 56. Since spring end 56 is constrained from movement in a direction 64 because of its position in step 62, so too is the needle guard 16 constrained from movement, thus insuring the needle is not re-exposed.

Turning now to FIGS. 6A to 6E, these figures illustrate a second embodiment of a locking mechanism. The overall structure and operation of this embodiment is similar to that shown and described above with respect to the embodiment of FIGS. 1 through 5, that is, the overall structure of the needle guard, the needle 22, the needle hub 24 as well as hub spring 30 is as described in reference to FIG. 3A and through FIGS. 4A to 4D. Thus, the foregoing will be assumed to be incorporated into the housing 100 and needle guard 102 of FIG. 6A. The assembly 104 on the proximal end of housing 100 is also similar in design and operation to that shown in the first embodiment. The needle guard 102 is slidable in directions 106 and 108 within the housing 100. The needle guard may have one or more ribs or other protrusions 110 and 112 which are fixed to or formed with the needle guard to keep the needle guard on a track or tracks. The interior of the housing 100 may have one or more slots 114 and 116 which mate with the ribs 110 and 112. This arrangement constrains the needle guard to movement in directions 106 and 108. According to another embodiment of the present invention, the ribs 110 and 112 may be part of housing 100 and track or tracks 114 and 116 may be part of the needle guard. A needle guard spring 118 is contained within the housing and located distally of the portion 120 of the assembly 104 and proximally of the proximal end 122 of the needle guard 102. A locking ring 124 (shown also in FIG. 7A and FIG. 8C) includes one or more locking pins 126, 128. The locking ring is positioned distally of the distal end 130 of the spring 118. The locking pins 126 and 128 (shown as two only for the purposes of illustration and may be of any suitable number) ride within slots 132, 134 (again, two being shown but may be any number of suitable slots). The distal end of each of the slots 132, 134 includes one or more inclined portions 136 and 137 and one or more steps 138 and 139. As can be seen in simplified FIGS. 8A and 8B, the inclined portions 136 and 137 are of the opposite angles so that the locking pins 126 and 128 are rotated about the locking ring 124 axis under the influence of the inclined portion 136 and 137 and then drop into a locking position and in contact with steps 138 and 139 while the needle guard 102 is pressed in direction 108.

Figure 6C:
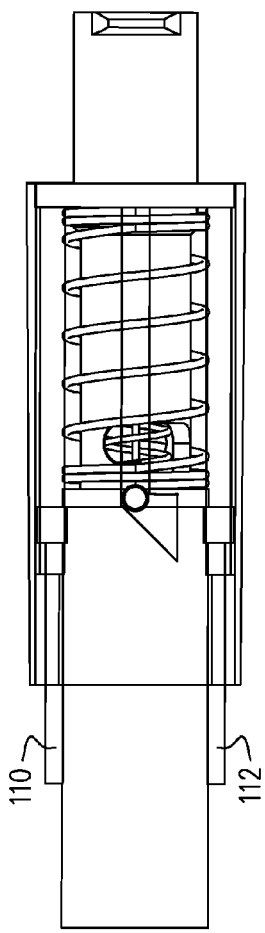
Figure 6D:
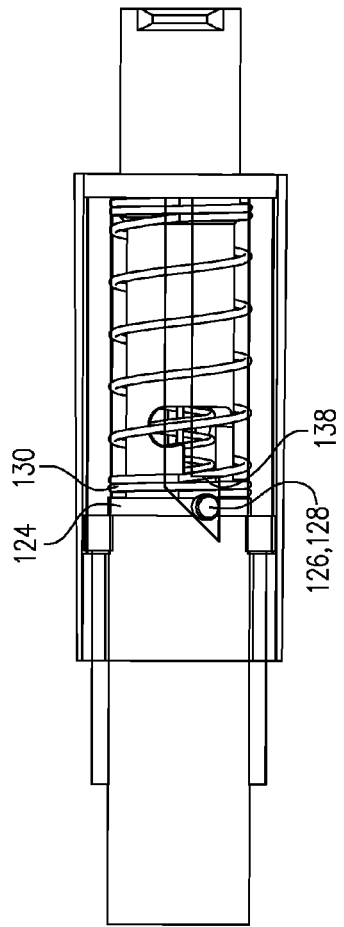
Figure 6E:
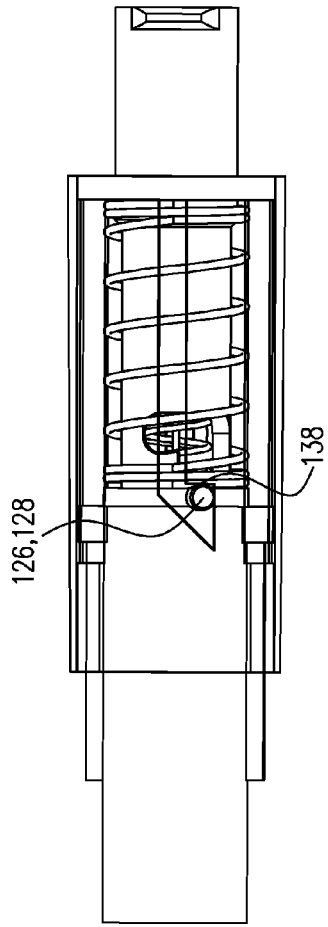
Figure 8A:
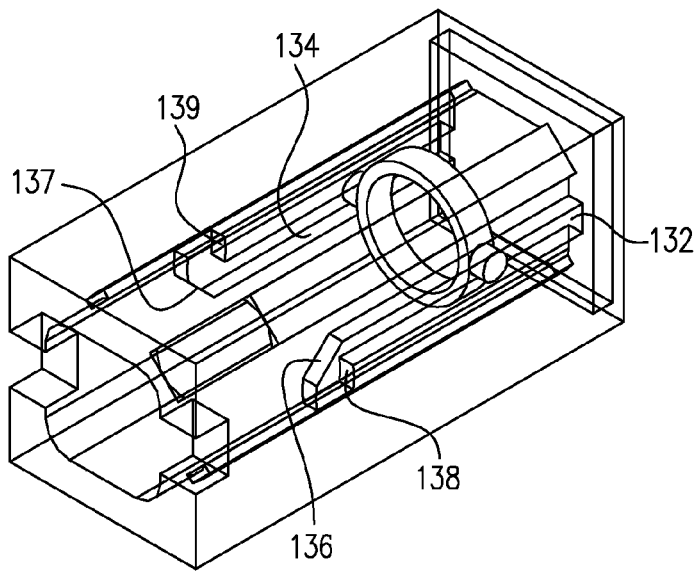
FIGS. 8A to 8C illustrate a locking mechanism used in conjunction with the embodiment of FIGS. 6A to 6E.
Figure 8B:
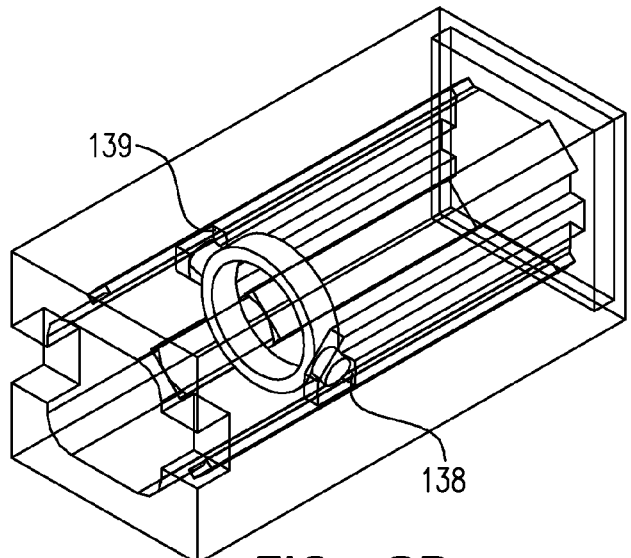
Figure 8C:
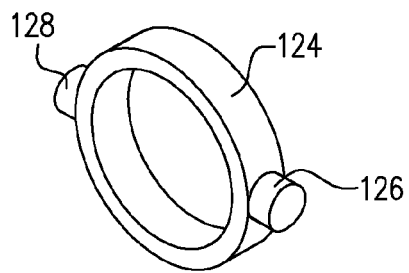

Now, illustrating the operation of the locking device of the present embodiment, FIG. 6A shows the assembly in a position similar to that shown in FIG. 3A in which the needle device is in a state prior to use (its first extended position as discussed above). FIG. 6B shows the positioning of elements during use and is similar to that shown in FIG. 3B (retracted position) however the exposed needle is not shown. In FIGS. 6C to 6D, the assembly is in the withdrawing position, that is, after injection has taken place and the syringe and needle assembly is moved away from the patient's skin (second extended position of the needle guard). FIG. 6E shows locking pin 128 pressed against stop 138 in case that needle guard 102 is pressed in direction 108. As the needle guard 102 moves in direction 106 under the influence of spring 118, the spring pushes the needle guard and the locking ring 124 in direction 106. In FIG. 6C, the locking pins 126,128 approach inclined portions 136 within the slots 132,134. Further movement of the needle guard in direction 106 causes the locking pins 126,128 to engage surfaces 136 and be pushed into step 138 as illustrated in FIGS. 6D and 6E. The needle is now covered by needle guard 102. Any pressure on the distal portion of the needle guard 102 in direction 108 will be stopped as the locking pins are fixed in steps 138, 139, thus preventing needle exposure. FIGS. 7A to 7E provide an alternative view of that illustrated in FIGS. 6A to 6E. Simplified FIG. 8C shows a detailed view of the locking ring 124 and FIGS. 8A and 8B show the interaction of the locking ring, the locking pins, the slots 132 and 134 and the steps 138 from a different perspective view. The housing is presented here in two parts only for easier manufacturing. It can be either produced in a unitary single part—or it can be separated into two or more parts in a different way than presented here.

In another aspect of the present invention, a pair of side-to-side symmetric windows may be provided to allow a user to view the tip of a needle. Examples of such windows may be seen in FIGS. 10A to 10D, discussed below. While shown as two windows, any number of windows may be provided, including a single window. In any case, the aforesaid U.S. Pat. Nos. 7,901,382 and 8,328,765 disclose such window structures. One purpose of providing such windows is to allow a user to view the needle tip when priming the needle prior to injection in a known manner. Another is to allow primed medication to be expelled from a housing with which the needle may be stored.

Figure 10A:
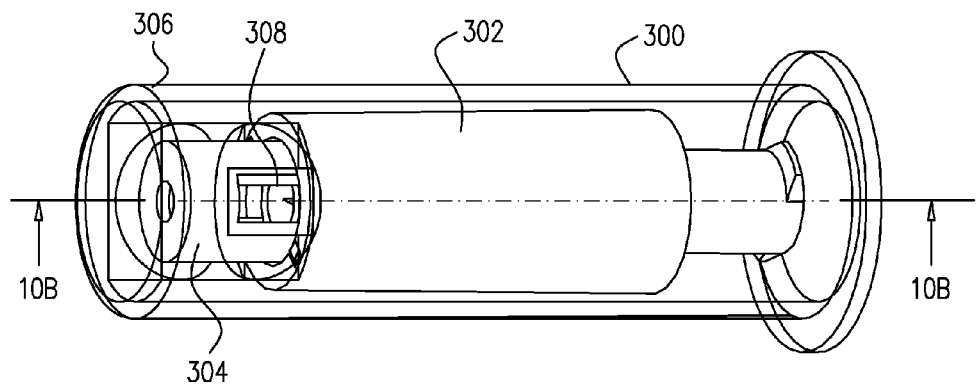
FIGS. 10A to 10E illustrate a container structure for the needle injection device with viewing apparatus.
Figure 10B:
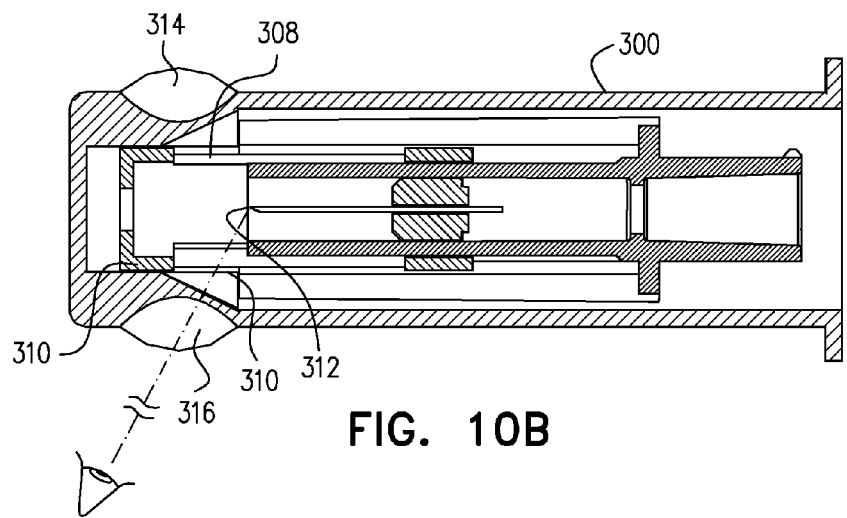
Figure 10C:
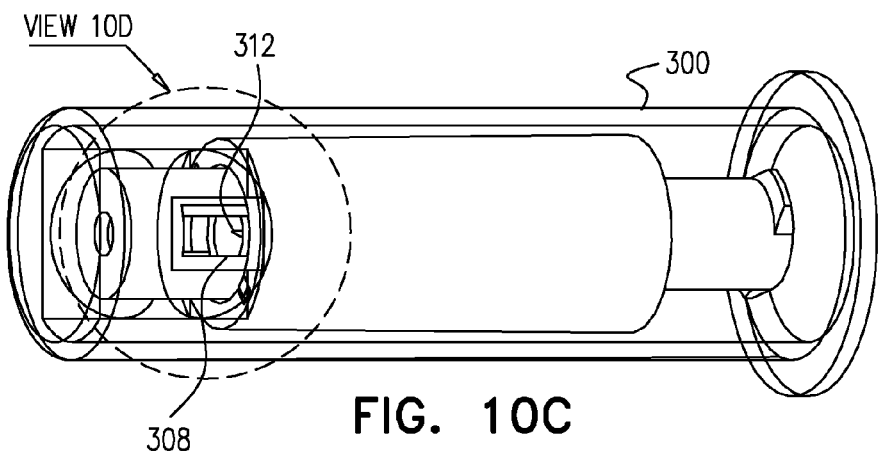
Figure 10D:
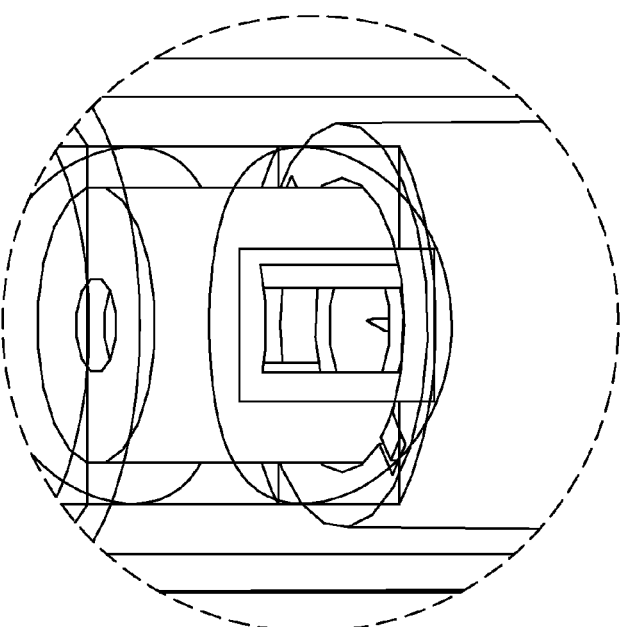
Figure 10E:
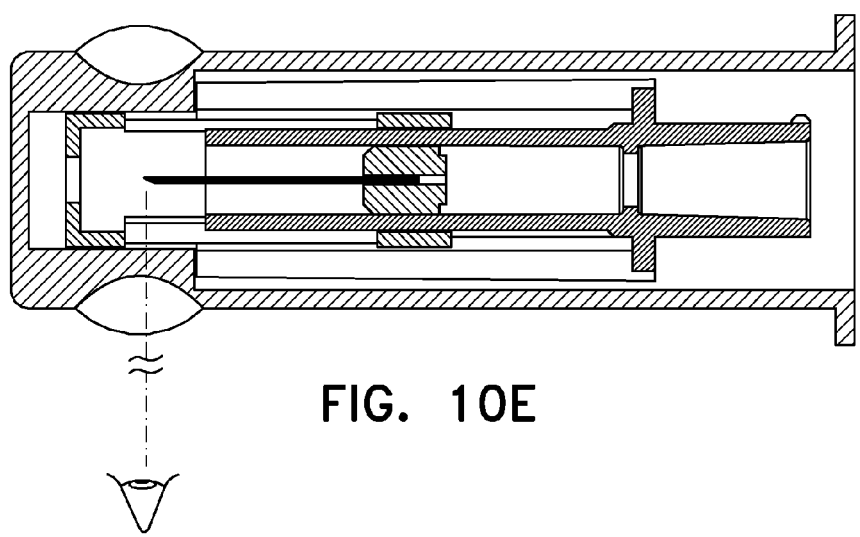

Turning now to FIGS. 10A to 10D, these figures illustrate the provision of an outer housing container 300 in which the automatic needle apparatus 302 of, for example, FIG. 3C may be contained. FIG. 10A shows the automatic needle apparatus inserted into container 300 such that the distal end 304 of the apparatus 302 is located in the distal end 306 of the container 300. The distal end 304 of the needle apparatus is shown as being a needle guard that may be constructed in a manner similar to the needle guard 16 shown in FIG. 4A, except that the needle guard 304 has two opposed openings 308 (visible) and 310 (not visible) that allow viewing of a needle tip 312, as best seen in blow-up FIG. 10D. While the shape of the openings 308 and 310 are shown as being of a rectangular polygonal shape it is to be understood that they may be in any shape desired to achieve viewing of needle tip 312. In addition, there could be only one opening 308 or any number more than two. Furthermore, the needle guard 304 can be made of a transparent material such that there will be no need for such openings. Such openings or transparency can be also designed on the housing of the automatic needle apparatus 302 (either in addition to the openings/transparency of the needle guard, or instead). Turning now to FIG. 10B, shows a section view of the container 300 of FIG. 10A rotated ninety degrees. In this view, it is seen that two lenses 314 and 316 are attached or otherwise fixed towards the distal end of the container and positioned to be in alignment with the windows 308 and 310 so that the user may see a magnified view of the needle tip 312. The lenses may be separate elements which are fixed to the container 300 or may be integrally molded into the container when the container is formed of a suitable plastic material. The container itself may be formed of a transparent material. Such an arrangement permits the lenses 314 and 316 to be integrally formed with the container by molding or other construction. The shape of the lens may be chosen to direct the optical path to the location of the needle tip 312. Each of the lenses can be provided with a prism, thus allowing directing the optical path to the needle tip 312, even in cases in which the needle tip is otherwise hidden from direct view. Such design allows the user to look, e.g., from a side view, perpendicular to the longitudinal axis of the needle device apparatus 302, as he or she will intuitively do, and see the needle tip 312 which may be otherwise hidden inside. Alternatively, the lenses may be provided without prisms as can be seen in FIG. 10E, for those situations in which the needle is viewable from a side view.

Figure 11A:
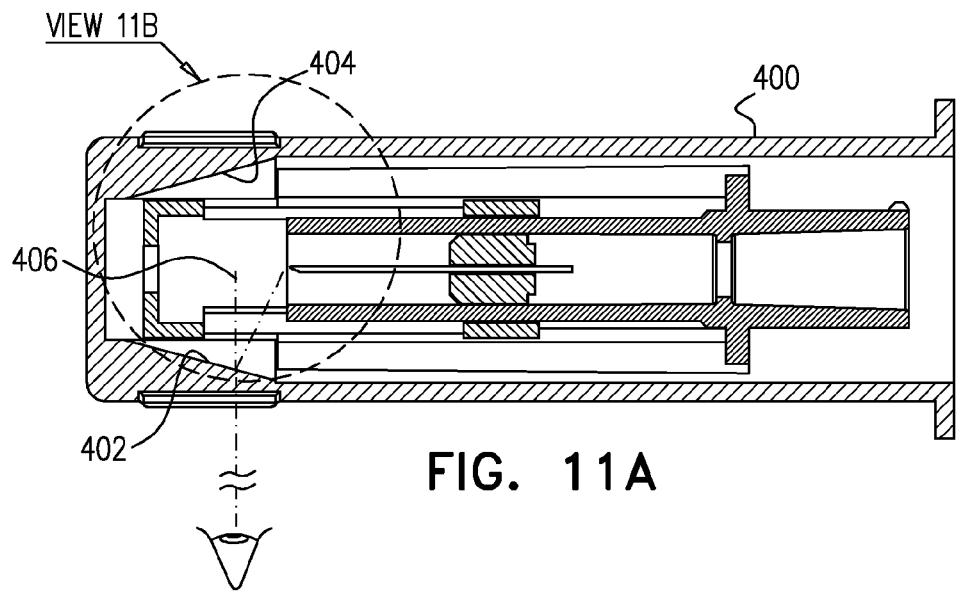
FIGS. 11A and 11B illustrate another embodiment of the container structure of FIGS. 10A to 10D.
Figure 11B:
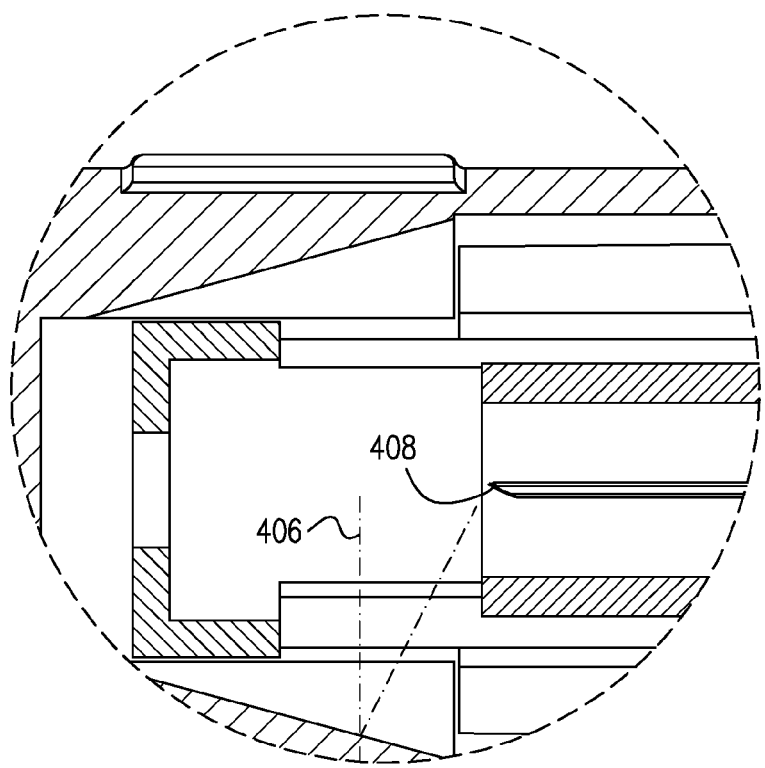

Turning now to FIGS. 11A to 11B, these figures illustrate a container structure similar in many respects to those illustrated in FIGS. 10A to 10D, except as follows. FIG. 11A shows a container 400 similar to the container 300 of FIG. 10B, except that in place of the particular lenses 314 and 316, a set of prisms 402 and 404 are attached to or otherwise formed in the distal portion of the container 400. As best seen in FIG. 11B, the optical path 406 is refracted by the prism 402 so as to direct the optical path 406 towards the needle tip 408 allowing easy viewing of the needle tip for the purposes discussed above. Furthermore, the interiors of the containers of either or both of FIGS. 10A-10D and FIGS. 11A to 11B, may contain an aligning mechanism, in the form of ribs or rails by way of example only, that interact with the automatic needle device so that when the device is inserted into the container, the apertures on the needle guard will align with the apertures on the container so that the needle distal end is visible. The lenses and/or prisms may be otherwise part of the needle guard or the housing or any other part of a needle device rather than the container.

Figure 12A:
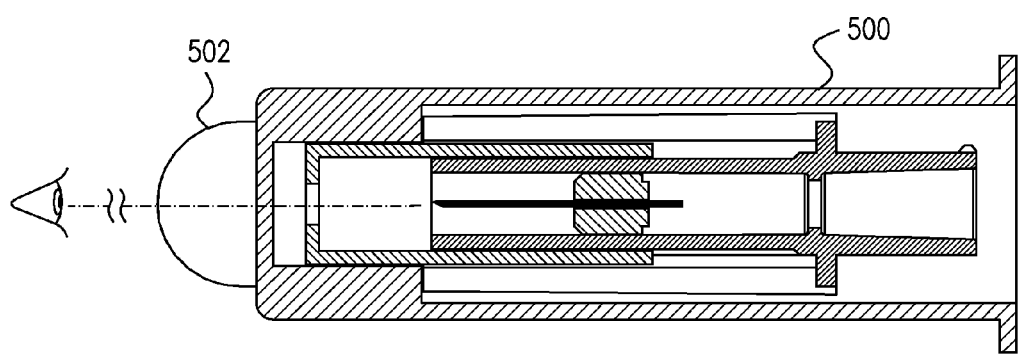
FIGS. 12A, 12B, illustrate yet another embodiment of the container structure of FIGS. 10A to 10D.
Figure 12B:
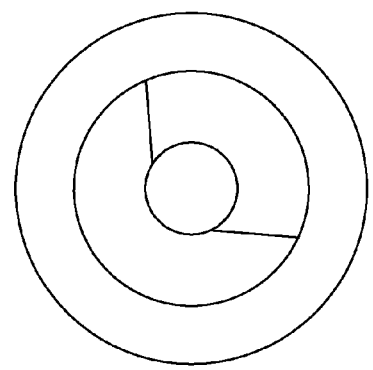
Figure 13A:
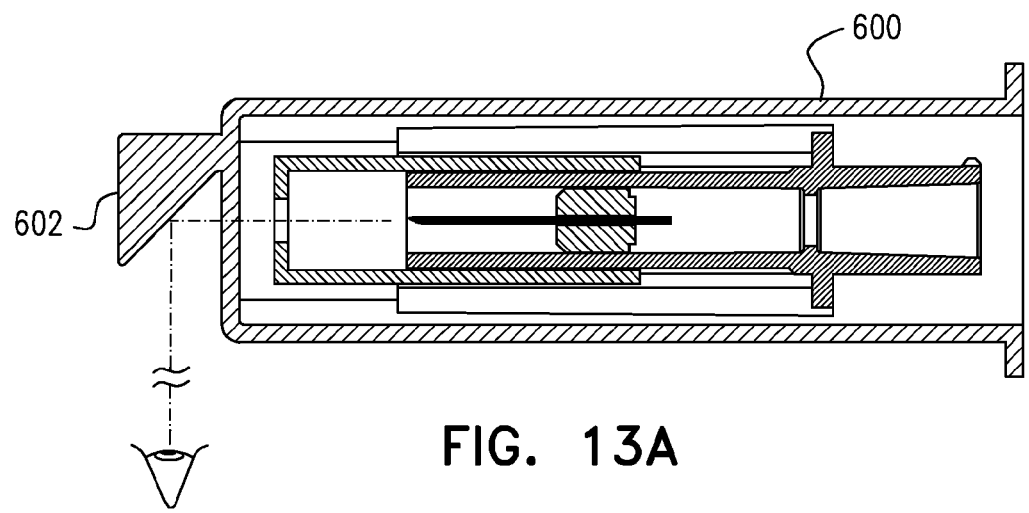
FIGS. 13A and 13B illustrate yet another embodiment of the container structure of FIGS. 10A to 10D.
Figure 13B:
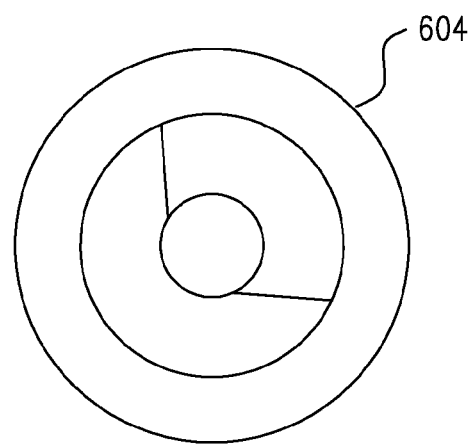

Turning now to FIGS. 12A, 12B, 13A and 13B, these figures are of other embodiments in which the needle may be viewed "end on" optically. In FIG. 12A, the container 500 has at its distal end a transparent lens, either formed integrally with the container 500 or separately attached, which allows a user to view the needle end on, as seen in FIG. 12B. The lens 502 may be of a suitable shape to magnify the image of the needle distal end contained within the container 500. In FIGS. 13A and 13B, the container has attached or formed at its distal end a right prism 602 that allows a user to view the distal end of the needle "end on", as seen in FIG. 13B. The right prism may be formed as part of the container or separately attached. In addition, an angled mirror may be substituted for the right prism. As with the embodiments of FIGS. 10A to 10E, the entire container 500 in FIGS. 12A to 12B, as well as FIGS. 13A to 13B, may be made of a transparent material. This would allow the lens 502 and the prism 602 to be formed integrally with their respective containers.

Although various features of the present invention may be described in the context of a single embodiment, it is to be understood that the features may also be provided separately or in any suitable combination, and vice versa. Furthermore, it is to be understood that the inventions herein may be carried out or practices in various ways and that the present invention can be implemented in embodiments other than the ones disclosed in the present application. It is also to be understood that the automatic needle device can be used for injections into, e.g., infusion bags, and not into a patient's skin as described above.

Some examples of variations of some of the features of the present invention include one or more of the following, individually or taken together:

The needle guard spring can be a coil spring, an elastomeric spring, a non-coil spring made of metallic, plastic or any other material The needle guard spring can have any number of offset coils at one or both ends, or in any position along the spring length, the offset coils having any pitch Instead of offset coils, the needle guard spring can have different shapes formed from the spring wire which extend radially outwardly or inwardly from the main spring body; In case the shape extends inwardly, it may lock against an inner housing element rather than an outer housing element.

The locking ring's one or more pins can be shaped as any protrusion, either polygonal or curved shape;

Instead of locking pins, the locking ring can be shaped with grooves or slots which lock against protrusions or ribs formed either in an outer element or an inner element;

The locking ring can be of a circular, rectangular, square or any other shape. In case the locking ring is other than circular shape, it can lock against another part by rotation of either the part or the ring such that it abuts a step(s) formed in the part.

The locking ring can also lock by sliding sidewardly into a groove or a step formed in a housing or another part of the needle assembly.

What we claim is:

1. An automatic needle device attachable to an injection device comprising:
   a housing element having distal and proximal ends;
   the proximal end of the housing element having a connector adapted for attachment to the injection device;
   a needle assembly at least partly within the housing element, the needle assembly having a needle extending from the distal end of the needle assembly;
   a needle guard having distal and proximal ends, the needle guard being positioned in the distal end of the housing element and movable from a first extended position to a retracted position to a second extended position, the needle guard covering the needle in the first and the second extended positions and exposing the needle in the retracted position;
   the needle guard being biased by a biasing device in a distal direction and being retracted to the retracted position upon contact of the distal end of the needle guard with a surface;
   the biasing device comprising a spring having distal and proximal ends;
   a locking mechanism, the locking mechanism locking the needle guard in the second extended position when the needle guard, under the influence of the biasing device, moves to the second extended position; and,
   wherein the spring distal end pushes the proximal end of the needle guard and is positioned in an interior locking surface within the housing element when the needle guard moves to the second extended position, whereby the needle guard is locked in the second extended position;
   wherein said spring is a coil spring having one or more of the coils in the distal end of the coil spring offset from the remaining coils of the coil spring, the one or more offset coils being positioned in the interior locking surface within the housing unit, when the needle guard moves to the second extended position.

2. The device of claim 1 wherein the one or more of the offset coils in the distal end are of a tighter pitch compared to the remaining coils of the second coil spring.

3. The automatic needle device of claim 1 wherein the needle guard additionally comprises a plurality of side walls connecting the distal end and the proximal end and wherein the side walls are apertured with at least one opening in at least one of the side walls to allow a user to view the needle distal end.

4. The device of claim 3 wherein the openings are one of: polygonally or curved shaped.

5. The automatic needle device of claim 1 wherein the needle guard additionally comprises a plurality of side walls connecting the distal end and the proximal end and wherein at least one of the needle guard side walls are of a substantially transparent material to allow a user to view the needle distal end.

6. An automatic needle device attachable to an injection device comprising:
   a housing element having distal and proximal ends;
   the proximal end of the housing element having a connector adapted for attachment to the injection device;
   a needle assembly at least partly within the housing element, the needle assembly having a needle extending from the distal end of the needle assembly;
   a needle guard having distal and proximal ends, the needle guard being positioned in the distal end of the housing element and movable from a first extended position to a retracted position to a second extended position, the needle guard covering the needle in the first and the second extended positions and exposing the needle in the retracted position;

the needle guard being biased by a biasing device in a distal direction and being retracted to the retracted position upon contact of the distal end of the needle guard with a surface;

the biasing device comprising a spring having distal and proximal ends;

a locking mechanism, the locking mechanism locking the needle guard in the second extended position when the needle guard, under the influence of the biasing device, moves to the second extended position; and the spring distal end pushes against a locking element proximal surface, the locking element distal surface pushing the needle guard proximal end, the locking element further comprising one or more locking protrusions engaging an interior surface within the housing when the needle guard moves to the second extended position, whereby the needle guard is locked in the second extended position;

and wherein the one or more locking protrusions slide within one or more corresponding grooves within the interior surface of the housing element, the one or more grooves each having a slot at the distal end of the one or more grooves, each slot receiving the one or more locking protrusions when the needle guard moves to its second extended position.

7. The device of claim 6 wherein the one or more locking protrusions comprises two locking protrusions and the one or more grooves comprises two grooves and wherein the locking protrusions are moved in a distal direction and axially turned to be positioned into two slots to lock the needle guard.

8. The automatic needle device of claim 6, wherein the needle guard additionally comprises a plurality of side walls connecting the distal end and the proximal end and wherein the side walls are apertured with at least one opening in at least one of the side walls to allow a user to view the needle distal end.

9. The automatic needle device of claim 6, wherein the needle guard additionally comprises a plurality of side walls connecting the distal end and the proximal end and wherein at least one of the needle guard side walls are of a substantially transparent material to allow a user to view the needle distal end.

* * * * *